United States Patent [19]

Rooks, II et al.

[11] 4,357,322
[45] Nov. 2, 1982

[54] METHOD OF PREVENTING, REDUCING OR INHIBITING INFLAMMATION

[75] Inventors: Wendell H. Rooks, II; Neil R. Ackerman, both of Los Altos; Albert J. Tomolonis, Cupertino, all of Calif.

[73] Assignee: Syntex (U.S.A.) Inc., Palo Alto, Calif.

[21] Appl. No.: 173,311

[22] Filed: Jul. 29, 1980

[51] Int. Cl.³ .................... A61K 37/02; C07C 103/52
[52] U.S. Cl. ............................ 424/177; 260/112.5 R
[58] Field of Search ................ 260/112.5 R; 424/177, 424/88, 92

[56] References Cited

U.S. PATENT DOCUMENTS

| 4,082,735 | 4/1978 | Jones et al. | 260/112.5 R |
| 4,082,736 | 4/1978 | Jones et al. | 260/112.5 R |
| 4,101,649 | 7/1978 | Adam et al. | 260/112.5 R |

FOREIGN PATENT DOCUMENTS 6068 12/1979 European Pat. Off. .

OTHER PUBLICATIONS

Chedid et al., Proc. Natl. Acad. Sci., U.S.A., vol. 74, pp. 2089-2093, 1977.

*Primary Examiner*—Blondel Hazel
*Attorney, Agent, or Firm*—James M. Kanagy; Alan M. Krubiner; Tom M. Moran

[57] ABSTRACT

Inflammation is prevented, reduced or inhibited by administering muramyl and desmethylmuramyl dipeptides of the general formula:

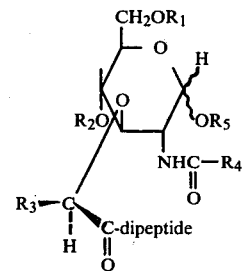

wherein each of $R^1$ through $R^5$ can independently be hydrogen or a variety of substituted or unsubstituted acyl, alkyl, aryl, or arylalkyl substituents. Pharmaceutical compositions containing such compounds useful for reducing inflammation are described.

8 Claims, No Drawings

METHOD OF PREVENTING, REDUCING OR INHIBITING INFLAMMATION

BACKGROUND OF THE INVENTION

1. Field of the Invention

The present invention is concerned with pharmaceutical compositions and methods for preventing, inhibiting or reducing inflammation in humans or in domestically useful animals, using muramyl peptides. More specifically, acylmuramyl and acyl desmethylmuramyl dipeptides are particularly useful.

2. Prior Art

Anti-inflammatory activity has been demonstrated for compounds representing a number of structural classes; for example, the corticosteroids, aspirin and related compounds, derivatives of aryl acetic and aryl pyruvic acid and relatives of phenylbutazone. However, no representative of any of these classes is regarded as ideal.

It has recently been found that crude acetylated glycoprotein cell wall fragments from a number of bacteria can be used to reduce inflammation (French Pat. Nos. 2,396,018; 2,396,020, and 2,405,298, and U.S. Pat. No. 4,154,821).

The anti-inflammatory activity of glucosamine in the gastro-intestinal tract has been described in U.S. Pat. No. 4,006,224. Japanese Pat. No. 54/055455 describes the anti-inflammatory and analgesic activity of glucosamine acylated with a 2-(p-isobutylphenyl)propionyl moiety. The zinc salts of acetylated or unacetylated glucosamine which is also the acetal derivative of an alkyl mercaptan are anti-inflammatory, according to Japanese Pat. No. 53/031627. Acetyl glucosamine is useful in treatment of degenerative articular diseases, as disclosed in French Pat. No. 2,016,182.

The invention herein relates to the surprising finding that a class of compounds, muramyl and desmethylmuramyl dipeptides heretofore useful only as adjuvants, possesses anti-inflammatory activity. This result is particularly unexpected because inflammation is a frequent side effect of adjuvant compounds; "adjuvant arthritis", in fact, forms the basis for a secondary screening test for anti-inflammatory agents. (Hirschelmann, et al, Wiss. Martin Luther Univ-Halle-Wittenberg-Math, Naturwiss. Reihe. 27(6) 35–49 (1978)).

The seminal work in this class of compounds, as assayed by their adjuvant activity was the preparation, by Merser et al, of N-acetylmuramyl-L-alanyl-D-isoglutamine. (Biochem. Biophys. Res. Commun. 66:1316, 1975). This compound, also known as MDP, was shown to be the minimal adjuvant structure which could substitute for mycobacteria as Freunds Complete Adjuvant. Ellouz et al, (Biochem. Biophys. Res. Commun. 59:1317, 1974).

Previous patents have described the preparation and use as adjuvants of muramyl and desmethylmuramyl dipeptides which are variations on a general formula:

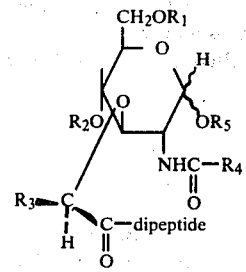

where each of $R_1$ through $R_5$ can independently be hydrogen or a variety of acyl, alkyl, aryl, or arylalkyl substituents any of which may be further substituted. Such compounds have been described in the following patents: Belgian Pat. Nos. 834,753; 834,754; 847,103; 849,214; German Pat. Nos. 2,710,455; 2,922,533; 2,747,379; 2,912,865; French Pat. Nos. 2,355,505; 2,358,159 and 2,375,249; European Patent Office Pat. Nos. 4,512 and 2,677; Japanese Pat. Nos. 54/063016; 54/073729 and 55/019236 and U.S. Pat. Nos. 4,082,735 and 4,082,736.

SUMMARY OF THE INVENTION

One aspect of this invention is a method for preventing, inhibiting or reducing inflammation in a mammal, which method comprises administering a therapeutically effective amount of a compound selected from those represented by the formula:

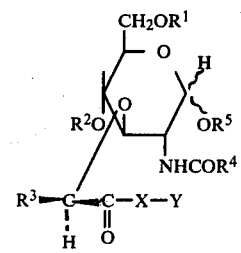

wherein:

$R^1$ and $R^2$ are the same or different and are hydrogen or optionally substituted acyl, $R^3$ is hydrogen or lower alkyl, $R^4$ is optionally substituted aryl or optionally substituted alkyl, $R^5$ is hydrogen or optionally substituted aryl or optionally substituted alkyl, X is an amino acyl moiety, Y is D-glutamic or D-aspartic acid, or a mono-, di-, or mixed alkyl ester, amide, or lower alkyl amide thereof.

By "mixed", is meant, for example, the case wherein one carboxyl is in the form of the amide, and the other, the ester.

Another aspect of the invention is a pharmaceutical composition useful for preventing, inhibiting or reducing inflammation in a human being or in domestically useful animals, which composition comprises a pharmaceutically acceptable, non-toxic carrier and a therapeutically acceptable amount of a compound of Formula A as described above.

FURTHER DESCRIPTION OF THE INVENTION

As used herein:

"alkyl" means a saturated branched or unbranched hydrocarbon chain containing 1–22 carbon atoms;

"lower alkyl" means a branched or unbranched saturated hydrocarbon chain containing 1–4 carbon atoms;

"acyl" means

where "R" is alkyl as herein defined;

"aryl" means phenyl or phenyl lower alkyl, e.g. benzyl;

"substituted" means the presence of —OH, —OR$^6$,

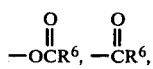

—NH$_2$, —NHR$^6$, or —N(R$^6$)$_2$ wherein "R$^6$" is lower alkyl as herein defined; and "aminoacyl" refers to an α-amino acid containing less than 12 carbon atoms.

The wavy lines represent the α or β configuration or mixtures thereof; if one wavy line is α the other is β.

A preferred class of compounds useful in the method and composition of this invention includes those of formula (A), above, wherein X is selected from the group consisting of:
L-alanyl,
L-valyl,
L-leucyl,
L-isoleucyl,
L-α-aminobutyryl,
L-seryl,
L-threonyl,
L-methionyl,
L-cysteinyl,
L-phenylalanyl,
L-tyrosyl,
L-tryptophanyl,
L-lysyl,
L-ornithyl,
L-arginyl,
L-histidyl,
L-glutamyl,
L-glutaminyl,
L-aspartyl,
L-asparaginyl,
L-prolyl, or
L-hydroxyprolyl.

A more preferred class is that wherein X is selected from the above-enumerated specific amino acids, and wherein R$^1$ and R$^2$ are both hydrogen.

A still more preferred class is that wherein:
R$^1$ and R$^2$ are both hydrogen;
R$^4$ is methyl or phenyl;
R$^5$ is hydrogen or optionally substituted phenyl;
X is L-alanyl;
Y is D-glutamic acid or a mono-, di-, or mixed alkyl ester, amide, or lower alkyl amide thereof.

The most preferred class is that wherein:
R$^1$ and R$^2$ are both hydrogen;
R$^3$ is either hydrogen or methyl;
R$^4$ is methyl;
R$^5$ is hydrogen;
X is L-alanyl; and
Y is either D-glutamic acid or D-isoglutamine.

Those compounds which are members of the most preferred class are
N-acetylmuramyl-L-alanyl-D-isoglutamine,
N-acetyl desmethylmuramyl L-alanyl-D-isoglutamine,
N-acetyl muramyl-L-alanyl-D-glutamic acid, and
N-acetyl desmethylmuramyl-L-alanyl-D-glutamic acid.

The effectiveness of these compounds in reduction of inflammation is shown by their success in standard laboratory tests. In particular, these compounds cause inhibition of inflammation induced by carrageenin injection into a rat's paw as shown according to the method of Winter et al *Proc. of the Soc. for Exptl. Biol. and Med.* 111, 544–547 (1962). This procedure is a recognized assay for anti-inflammatory activity within the dose range suitable for therapeutic administration of drugs.

The effective dosage is in the range of 0.01 mg/kg/day to 10 mg/kg/day; preferably between 0.5 and 5 mg/kg/day depending on mode of administration. Using this range of values, for a 70 kg individual this would translate to a dosage of 0.7 mg to 700 mg or preferably 7 mg to 350 mg per day. The dosage regimen may consist of unit or divided dosages, but in any event will necessarily be dependent upon the needs of the subject being treated, the severity of the affliction, and the judgment of the attending medical practitioner.

The embodiment of the invention relating to the pharmaceutical composition varies with the mode of administration, which may be topical, oral, parenteral, or systemic. In general, the composition will consist of 0.5% to 95% active ingredient and the remainder, suitable carrier. The composition containing the subject compound may be subjected to conventional pharmaceutical expedients such as sterilization (e.g. by millipore filtration) and can contain conventional pharmaceutical excipients such as preservatives, stabilizing agents, emulsifying agents, bulking/binding agents, salts for the adjustment of osmotic pressure, or buffers. The composition may also contain other therapeutically useful materials, or materials which prolong the duration of action of the present compound. Actual methods of preparing such dosage forms are known or will be apparent to those skilled in the art. An extensive compilation of such formulation techniques may be found, for example, in "Remington's Pharmaceutical Sciences" by E. W. Martin, 15th Ed., (1975) Mack Publ. Co.

In any event, the pharmaceutical composition to be administered will contain a quantity of compound in a therapeutically effective amount for treatment of the particular condition of concern as the active ingredient.

For topical administration, these compositions comprise an effective amount of a compound of this class in admixture with a pharmaceutically acceptable non-toxic carrier. A suitable range of composition would be 0.1%–10% active ingredient, and the balance carrier, preferably 1–2% active ingredient. The concentration of muramyl dipeptide in pharmaceutical compositions suitable for topical application will vary depending upon the particular activity of the compound used in conjunction with the condition and subject to be treated. Suitable carriers or medicament vehicles for topical application of these compounds include creams, ointments, lotions, emulsions, solutions and the like.

For example, a suitable ointment for topical application of compounds of the instant invention contains 15 to 45 percent of a saturated fatty alcohol having 16 to 24 carbon atoms such as cetyl alcohol, stearyl alcohol, behenyl alcohol, and the like and 45 to 85 wt. percent of a glycol solvent such as propylene glycol, polyethylene glycol, dipropylene glycol, and mixtures thereof. The ointment can also contain 0 to 15 wt. percent of a plasticizer such as polyethylene glycol, 1,2,6-hexanetriol, sorbitol, glycerol, and the like; 0 to 15 wt. percent of a coupling agent such as a saturated fatty acid having from 16 to 24 carbon atoms, e.g., stearic acid, palmitic acid, behenic acid, a fatty acid amide e.g., oleamide, palmitamide, stearamide, behenamide and an ester of a fatty acid having from 16 to 24 carbon atoms such as sorbitol monostearate, polyethylene glycol monostearate, polypropylene glycol or the corresponding monoester of other fatty acids such as oleic acid and palmitic acid; and 0 to 20 wt. percent of a penetrant such as dimethyl sulfoxide, dimethylacetamide, dimethylformamide, and the like.

For oral administration, these compositions contain an effective amount of a compound of this class incorporated in a mixture with any of the normally employed excipients such as, for example, pharmaceutical grades of mannitol, lactose, starch, magnesium stearate, sodium saccharin, talcum, cellulose, glucose, sucrose, magnesium carbonate and similar vehicles. The active ingredient comprises 25% to 95% of such formulations, preferably 25-70%. These compositions take the form of solutions, suspensions, tablets, pills, capsules, powders, sustained release formulations and the like.

For parenteral administration, compositions may consist of conventional forms such as solutions or suspensions ready for injection, dry products suitable for solution or suspension immediately prior to injection, or emulsions. A more recently described method of parenteral administration is via a slow-release implant type of formulation such as those generally known in the art, particularly those that are biosoluble or biodegradable.

Typical excipients for solid formulations include, e.g. magnesium stearate, starch, lactose, gelatin and the like; for liquid formulations there may be mentioned, e.g. polyalkylene glycols, water, oils of vegetable origin and low boiling solvents such as isopropanol and hydrogenated naphthalenes.

The percent of the subject compound in the composition will depend on the mode of administration, as well as other factors, since parenteral administration includes intramuscular, subcutaneous and intravenous routes. However, the active ingredient will, in any event, comprise 0.5% to 20%, or preferably 1-2% of such compositions.

Compositions for systemic administration are similar or identical to those for parenteral administration. These include liquids which can be sprayed into the nostrils, or solid suppositories which can be inserted buccally or rectally.

In the following specific examples the results of standard bioassays and typical compositions are described. It should be recognized by those skilled in the art that the descriptions contained herein are only illustrative of the invention and should not be construed as limiting the scope or spirit of the invention in any manner.

The literature cited above and in the examples is hereby incorporated by reference and made a part hereof.

EXAMPLE 1

In vivo anti-inflammatory assay of N-acetyl-desmethylmuramyl-L-alanyl-D-isoglutamine The procedure is after the report by Winter et al (supra). Female rats, weighing 160-180 grams obtained from Hilltop Farms are used. The test materials are given at hour 0 orally or subcutaneously (SC) in 1 ml aqueous vehicle. At hour 1, 0.05 ml of a 1% solution (in 0.9% NaCl) of carrageenin is injected into the right hind paw. This injection causes inflammation of the paw. The rats are sacrificed at hour 4, at which time both hind paws are removed and weighed separately. The percent increase in paw size is calculated according to the formula:

$$\frac{\text{Wt. Right Paw} - \text{Wt. Left Paw}}{\text{Wt. Left Paw}} \times 100$$

The data obtained were as follows:

TABLE 1

| Test Material | Route | Dose mg | No. of Rats | Mean Increase in Paw Wt. % ± S.E. |
|---|---|---|---|---|
| Vehicle Control | Oral | — | 8 | 38.9 ± 2.2 |
| N—acetyl-des-methylmuramyl-L—alanyl-D—isoglutamine | Oral | 0.085 | 6 | 45.5 ± 5.0 |
|  |  | 0.85 | 6 | 31.2 ± 2.5 |
|  |  | 8.5 | 6 | 19.3 ± 3.1 |
| Vehicle Control | SC | — | 8 | 32.0 ± 3.0 |
| N—acetyl-des-methylmuramyl-L—alanyl-D—isoglutamine | SC | 0.085 | 6 | 19.1 ± 4.0 |
|  |  | 0.85 | 6 | 18.7 ± 3.7 |
|  |  | 8.5 | 6 | 21.3 ± 2.4 |

Thus, subcutaneous administration showed effectiveness at all levels above 0.5 mg/kg in the rat while oral administration required somewhat higher dosage.

Similarily, other compounds set forth hereinbefore; useful in the method of this invention, may be tested in analogous protocols.

In Examples 2-5, "active ingredient" refers to N-acetyl muramyl-L-alanyl-D-isoglutamine. However, any of the glycodipeptides referred to above may be utilized.

EXAMPLE 2

Topical Formulation

The composition contains:

|  | % wt./wt. |
|---|---|
| Active ingredient | 0.5 |
| Methyl paraben | 0.025 |
| Propyl paraben | 0.015 |
| Sodium lauryl sulfate | 1.0 |
| Propylene glycol | 12.0 |
| Stearyl alcohol | 25.0 |
| White petrolatum | 25.0 |
| Purified water qs. ad. | 100.0 |

The stearyl alcohol and white petrolatum are heated on a steam bath to about 75°. The other ingredients, previously dissolved in the water and warmed to 75°, are added with stirring. Stirring is continued until the mixture congeals.

EXAMPLE 3

Oral Formulation

The composition contains:

|  | % wt./wt. |
|---|---|
| Active ingredient | 95 |
| Lactose | 5 |

The materials are mixed and granulated and used to fill gelatin capsules containing 300 mg. each.

EXAMPLE 4

Parenteral Formulation

The composition contains:

|  | % wt./wt. |
|---|---|
| Active ingredient | 1.0 |
| NaCl | 0.9 |
| Sodium Carboxymethyl/cellulose | 0.5 |
| Polysorbate 80 | 0.4 |
| Benzyl alcohol | 0.9 |
| Water for injection qs. ad. | 100 |

The solution is sterilized by filtration before injection. Administration of approximately 4 ml would provide a dose of 40 mg.

EXAMPLE 5

Rectal Systemic Formulation (Suppository)

The composition contains:

|  | % wt./wt. |
|---|---|
| Active ingredient | 1% |
| Witepsol H-15 (triglycerides of saturated fatty acids - Riches-Nelson, N.Y.) | 99% |

The active ingredient is ground to a fine powder and suspended in the carrier. The mixture is then formed into a 2.8 gram suppository.

We claim:

1. A method for preventing, reducing or inhibiting inflammation in a human or domestically useful animal which comprises administration to a subject in need of such treatment, an effective amount of or pharmaceutical composition containing an effective amount of a compound selected from those represented by the formula:

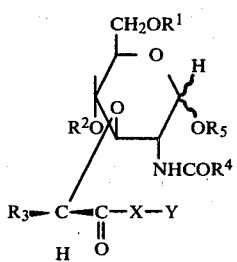

wherein:
$R^1$ and $R^2$ are the same or different and are hydrogen or optionally substituted acyl;
$R^3$ is hydrogen or lower alkyl;
$R^4$ is optionally substituted aryl or optionally substituted alkyl;
$R^5$ is hydrogen or optionally substituted aryl or optionally substituted alkyl;
X is an amino acyl moiety; and
Y is D-glutamic or D-aspartic acid, or a mono-, di-, or mixed alkyl ester, amide, or lower alkyl amide thereof.

2. The method of claim 1, wherein X is selected from the group consisting of:
L-alanyl,
L-valyl,
L-leucyl,
L-isoleucyl,
L-α-aminobutyryl,
L-seryl,
L-threonyl,
L-methionyl,
L-cysteinyl,
L-phenylalanyl,
L-tyrosyl,
L-tryptophanyl,
L-lysyl,
L-ornithyl,
L-arginyl,
L-histidyl,
L-glutamyl,
L-glutaminyl,
L-aspartyl,
L-asparaginyl,
L-prolyl, or
L-hydroxyprolyl.

3. The method of claim 2 wherein $R^1$ and $R^2$ are hydrogen.

4. The method of claim 1, wherein:
$R^1$ and $R^2$ are hydrogen;
$R^4$ is methyl or phenyl;
$R^5$ is hydrogen or optionally substituted phenyl;
X is L-alanyl; and
Y is D-glutamic or a mono-, di-, or mixed alkyl ester, amide, or lower alkyl amide thereof.

5. The method of claim 1, wherein:
$R^1$ and $R^2$ are hydrogen,
$R^3$ and $R^4$ are methyl,
$R^5$ is hydrogen,
X is L-alanyl, and
Y is D-isoglutamine; i.e. N-acetylmuramyl-L-alanyl-D-isoglutamine.

6. The method of claim 3, wherein
$R^3$ is hydrogen;
i.e. N-acetyl desmethyl muramyl L-alanyl-D-isoglutamine.

7. The method of claim 4 wherein Y is D-glutamic acid;
i.e. N-acetylmuramyl-L-alanyl-D-glutamic acid.

8. The method of claim 4 wherein $R^3$ is hydrogen,
i.e. N-acetyldesmethyl muramyl-L-alanyl-D-glutamic acid.

* * * * *